(12) United States Patent
Huang

(10) Patent No.: US 8,513,000 B2
(45) Date of Patent: Aug. 20, 2013

(54) HIGH-THROUGHPUT CELL TRANSFECTION DEVICE AND METHODS OF USING THEREOF

(75) Inventor: Yong Huang, Milpitas, CA (US)

(73) Assignee: Rational Biotechnology, Inc., Menlo Park, CA (US)

( * ) Notice: Subject to any disclaimer, the term of this patent is extended or adjusted under 35 U.S.C. 154(b) by 451 days.

(21) Appl. No.: 12/799,105

(22) Filed: Apr. 15, 2010

(65) Prior Publication Data

US 2010/0305005 A1 Dec. 2, 2010

Related U.S. Application Data

(63) Continuation of application No. 12/658,950, filed on Feb. 16, 2010, which is a continuation of application No. 11/529,964, filed on Sep. 30, 2006, now Pat. No. 7,687,267.

(51) Int. Cl.
*C12M 1/18* (2006.01)

(52) U.S. Cl.
USPC .......... 435/285.2; 435/294.1; 435/297.5; 435/461; 435/470

(58) Field of Classification Search
None
See application file for complete search history.

(56) References Cited

U.S. PATENT DOCUMENTS

| | | | |
|---|---|---|---|
| 6,150,148 A | 11/2000 | Nanda et al. | |
| 6,300,108 B1 | 10/2001 | Rubinsky et al. | |
| 6,352,853 B1 * | 3/2002 | King et al. | 435/285.2 |
| 6,403,348 B1 | 6/2002 | Rubinsky et al. | |
| 6,544,790 B1 | 4/2003 | Sabatini | |
| 7,462,459 B2 | 12/2008 | Zerangue | |
| 7,687,267 B2 | 3/2010 | Huang | |
| 7,943,367 B2 | 5/2011 | Collins et al. | |
| 2005/0170510 A1 | 8/2005 | Huang et al. | |
| 2006/0121446 A1 | 6/2006 | Abassi et al. | |
| 2006/0142688 A1 | 6/2006 | Kon et al. | |
| 2006/0246572 A1 | 11/2006 | Ragsdale et al. | |
| 2008/0081372 A1 | 4/2008 | Huang | |
| 2008/0091135 A1 | 4/2008 | Draghia-Akli et al. | |
| 2008/0156640 A1 | 7/2008 | Collins et al. | |
| 2010/0196984 A1 | 8/2010 | Rubinsky et al. | |
| 2010/0279320 A1 | 11/2010 | Huang | |
| 2010/0317548 A1 | 12/2010 | Huang | |

FOREIGN PATENT DOCUMENTS

JP 2004/00147517 A1 5/2004

OTHER PUBLICATIONS

International search report and written opinion dated Feb. 22, 2011 for PCT Application No. US10/53279.
U.S. Appl. No. 13/502,334, filed Jun. 7, 2012, Huang et al.
Office action dated Mar. 27, 2013 for U.S. Appl. No. 13/502,334.
Office action dated Apr. 6, 2012 for U.S. Appl. No. 12/658,945.
Office action dated Aug. 18, 2009 for U.S. Appl. No. 11/529,964.
Office action dated Nov. 14, 2012 for U.S. Appl. No. 12/658,950.

* cited by examiner

*Primary Examiner* — Jim Ketter
(74) *Attorney, Agent, or Firm* — Wilson Sonsini Goodrich & Rosati

(57) ABSTRACT

Transfecting biology cells with nucleic acid molecules (DNA, siRNA) is an essential prerequisite in elucidating how genes function in complex cellular context and how their activities could be modulated for therapeutic intervention. Traditionally studies are carried out on a low throughput gene-by-gene scale, which has created a huge bottleneck in functional genomic study and drug discovery. Development of high-throughput cell transfection technology will permit functional analysis of massive number of genes and how their activities could be modulated by chemical or biological entities inside cells. This invention describes design, construction of device and apparatus for high throughput effective cell transfection. Procedures and protocols for using the device and apparatus are also described in the application. Novel methods of using the device in cell-based assays are also disclosed.

12 Claims, 20 Drawing Sheets

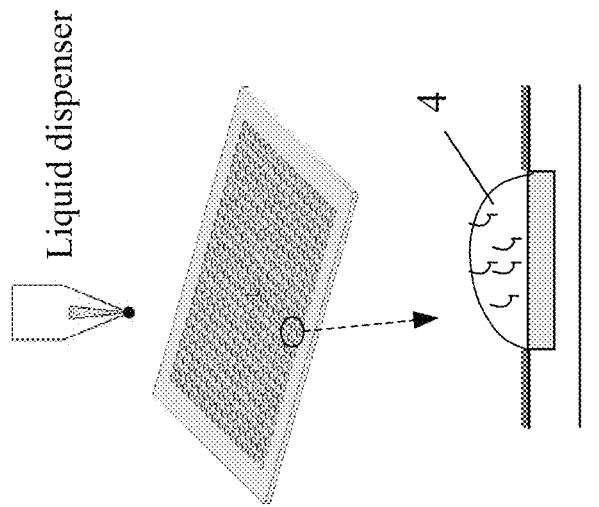
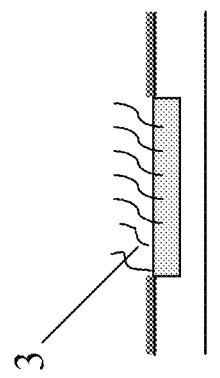
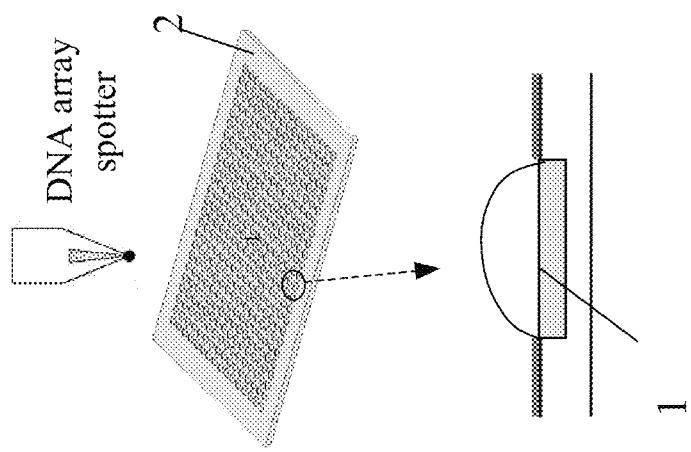
Fig. 7c
Fig. 7b
Fig. 7a

HIGH-THROUGHPUT CELL TRANSFECTION DEVICE AND METHODS OF USING THEREOF

CROSS-REFERENCE

This application is a continuation of application U.S. Ser. No. 12/658,950, filed Feb. 16, 2010, which is a continuation of application U.S. Ser. No. 11/529,964, filed Sep. 30, 2006, now U.S. Pat. No. 7,687,267, all of which are incorporated herein by reference in their entirety.

FIELD OF THE INVENTION

This invention relates to the biotechnology field in general and with specific reference to effective transfection of biological cells in a high throughput fashion, and its applications in drug discovery and development.

BACKGROUND OF THE INVENTION

Being able to effectively introduce foreign molecules, such as DNA, siRNA, protein, etc., into biological cells is of great importance in biology and biotechnology. Particularly effective transfection of biological cells with nucleic acid molecules is an essential prerequisite in elucidating how genes function in complex cellular context and how their activities could be modulated for therapeutic intervention. Cell transfection is routinely used in fundamental biology research and pharmaceutical development. Traditionally studies are normally carried out on a low throughput gene-by-gene scale, which has created a huge bottleneck in functional genomic study and drug discovery. Development of high-throughput cell transfection technology will permit functional analysis of massive number of genes and how their activities could be modulated by chemical or biological entities. Development of high-throughput cell transfection methods will significantly accelerate biology research and facilitate translation of genomic knowledge into therapeutic means in fighting various diseases.

Several methods are currently available for cell transfection, such as viral transduction, lipofection, electroporation, etc. Recombinant vectors derived from viruses are very effective in transfecting engineered cell lines and primary cells. However, use of viral vectors often results in undesirable alteration of cellular functions, in addition vector preparation is time-consuming and laborious, thus its application in high-throughput transfection is limited. Lipid based transfection methods are routinely used in high-throughput transfection applications, and a recent invention based on lipid transfection claims ultra-high-throughput capability [U.S. Pat. No. 6,544,790]. Nevertheless, all lipofection methods lack of ability of transfection non-dividing cells, particularly primary cells directly derived from animal tissue.

Electroporation is a process associated with transient permeabilization of cell membranes under electrical fields. It has been shown to be capable of delivering various substances (genes, siRNAs, antibodies, proteins and nanoparticles) into virtually any type of cells (engineered cell lines and primary cells). On the other hand, electroporation is often known for low efficiency, poor inconsistency, and extensive cell damage. This is largely due to the trial-and-error approach adopted by conventional electroporation systems, which apply hundreds to thousands of volts to cells suspended in solution, inevitably kill large portion of cells due to a process called irreversible electroporation.

Several novel methods and devices have been invented recently to address issues of low transfection efficiency and poor cell motility associated with electroporation [U.S. Pat. No. 6,300,108, U.S. Pat. No. 6,403,348, US2005/0170510]]. The related arts employ feed-back mechanisms to monitor electroporation in cells so to achieve high degree of transfection efficiency and high cell motility. The new methods and devices have been proven to be very useful in transfection of cells with a variety of foreign molecules. However, the design of the devices limit their capability of processing cells in high-throughput fashion, which is particularly required by cell-based assays for functional genomics study and drug discovery. Secondly, in the case of transfecting cells with DNA molecules, the related arts do not address effective delivery of DNA molecules into cell nuclei, which is required for cells to express proteins encoded by the DNA molecules. These and other needs are addressed by the transfection devices of the present invention. In addition, novel use of the disclosed transfection devices and methods in cell-based assays employing transient transfection is also presented in this invention.

BRIEF DESCRIPTION OF THE INVENTION

The present invention includes a high-throughput cell transfection device, methods for making and using the cell transfection device. The cell transfection device has two chambers separated by a thin porous membrane where cells can attach. Proper differential electric potential is generated across the cells residing on the porous membrane to electroporate the cells, thus permitting effective delivery of foreign molecules into the cells. The porous membrane can be treated to allow selective transfection of cells at particular location, leaving the rest of cells unaffected. A novel approach is also presented that permits realization of high-density electrical connections through convex liquid droplets, as well as means to form liquid droplets at selected locations. Methods for introducing foreign molecules to the cells in a high-throughput fashion are also presented. With the ability of transfecting cells in a high-throughput mode, we further describe methods that employ transfection of cells for profiling transcription factor activities in cells, and profiling influence of transporter proteins on transportation of molecules in and out of cells, and further their applications in drug discovery.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 7 is three schematic illustrations of a method for parallel loading of foreign molecules to a cell transfection device by pre-depositing the molecules on electrode pads.

DETAILED DESCRIPTION OF THE INVENTION

Before the present methods, treatments and devices are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a compound" includes a plurality of such compounds and reference to "the sample" includes reference to one or more samples and equivalents thereof known to those skilled in the art, and so forth.

CELL TRANSFECTION DEVICE AND APPARATUS

Cell Culture Device Design and Construction

Figure 1:
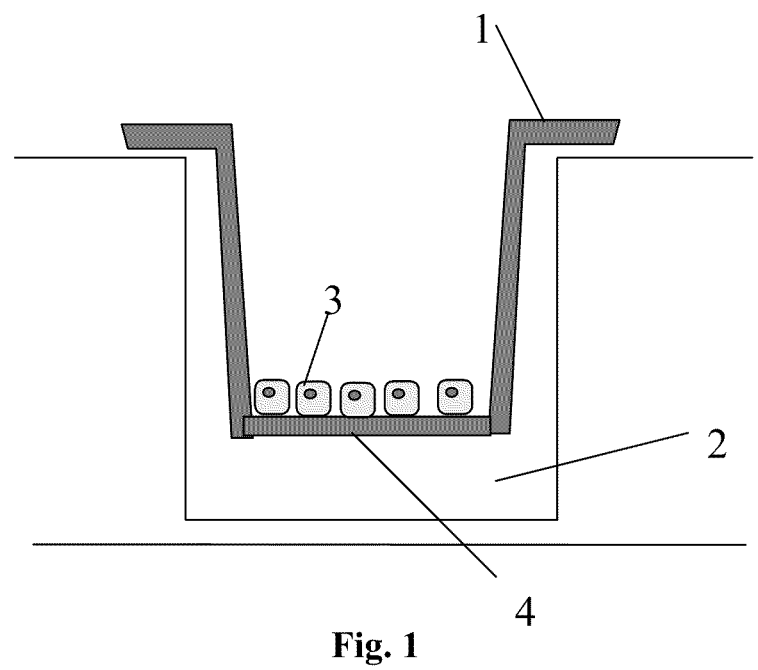
FIG. 1 is a schematic cross-section view of a traditional cell culture insert for growing cells on a porous membrane.
Figure 2:
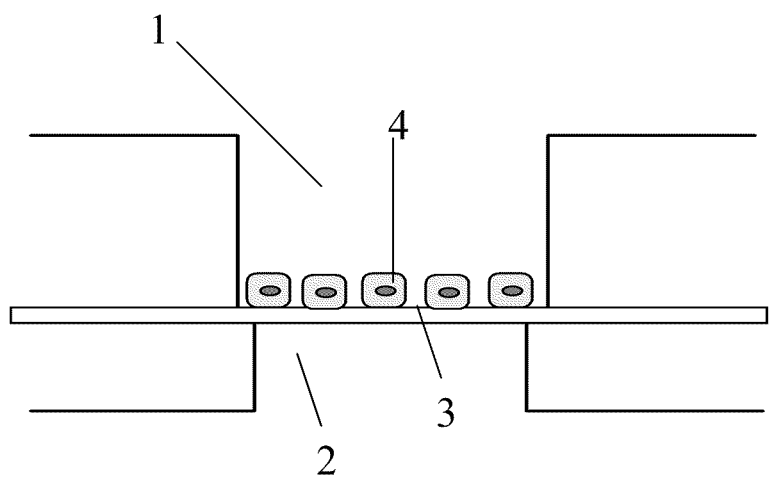
FIG. 2 is a schematic cross-section view of a novel cell culture device for growing cells on a porous membrane.

The cell transfection device described in the present invention is intended to transfect cells attached to a porous membrane, in a high-throughput fashion. To culture cells on a porous membrane, it requires feeding cells from both side of the porous membrane. Traditional ways to culture cells on a porous membrane involves use of cell culture insert (1) and a separate companion well (2), as depicted in FIG. 1. Cells (3) are introduced to the insert that has a porous membrane (4) where cells can attach. The drawback of this design is that it is difficult and costly to construct high-throughput device which normally contains more than 96 individual units on the industrial standard 5"×3.3" microtiter plate format. In the present invention, a cell culture device is depicted in FIG. 2. Unlike the conventional cell culture inserts, the described cell culture device has a first chamber (1), and a second chamber (2), and a porous membrane (3) separating the two chambers. Cells (4) can be introduced to any one of, or both chambers, and attach to either side, or both sides, of the porous membrane. It should be noted the simple geometry of the openings shown in FIG. 2 is for illustration, actual device can have more complex openings to serve specific purposes.

Figure 3:
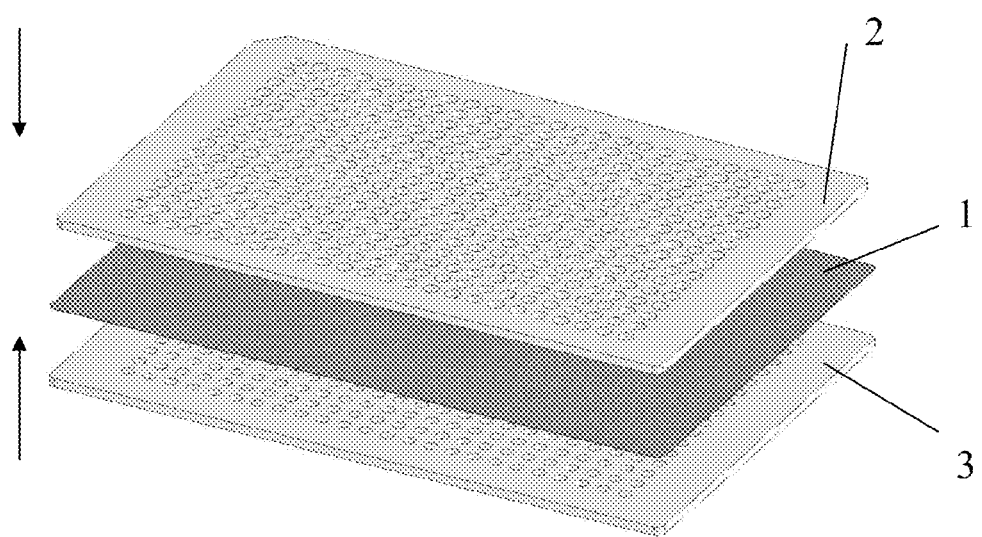
FIG. 3 shows a typical method of constructing the cell culture device of FIG. 2.

Because of the simplicity of the device, it is straight forward to multiply such devices in an array format for high-throughput applications. FIG. 3 illustrates a type construction process, a 24×16 array of openings in 384-well microplate footprint is presented for illustration purpose. A porous membrane (1) is first attached, using thermal welding or gluing, to a first rigid support plate (2) with an array of openings. The porous membrane is made of dielectric materials, including but not limited to, polycarbonate, PET, etc., with a film thickness from 1 um to 1 mm. The support plate is made of rigid and dielectric materials including but not limited to, plastic, glass, quartz etc., and is from 0.5 mm to 10 mm in thickness. The characteristic dimension of the openings of the support plate is between 0.1 mm to 10 mm. Then a second plate (3) with the same number of openings that are individually aligned with the openings of the first plate, is attached to the other side of the porous membrane, thus producing a cell culture plate with an array of cell culture devices depicted in FIG. 2. The second plate is also made of dielectric materials. It should be noted that the second plate can be substituted with a thin dielectric film with openings, or dielectric adhesive paste applied to the specific area of the porous membrane to expose specific area of the porous membrane under the openings of the first support plate.

Cell Transfection Device Design

Figure 4:
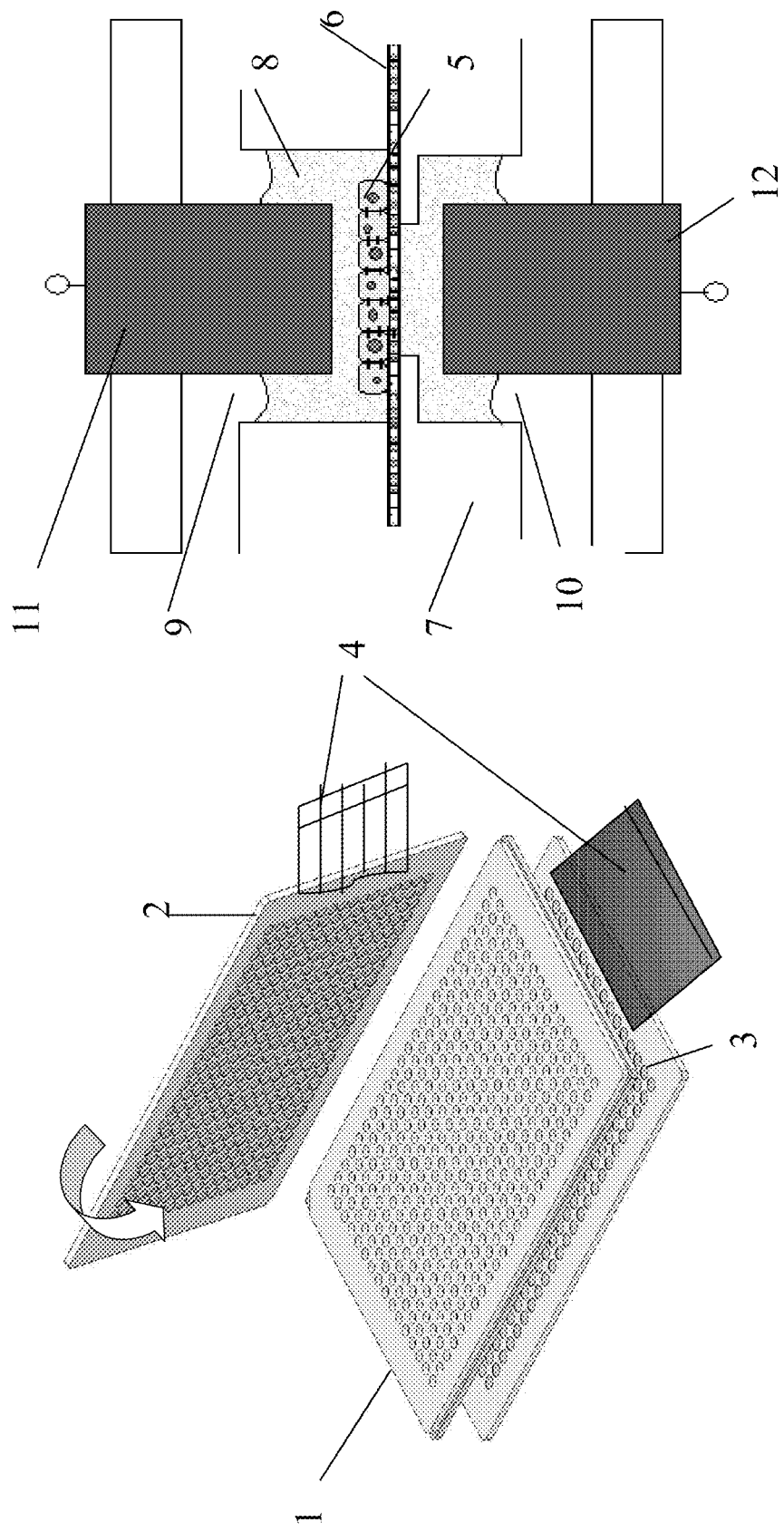
FIG. 4 is two schematic illustrations of a high-throughput cell transfection device containing an array of cell transfection units, and cross-section view of a typical cell transfection unit

The described cell transfection device employs electroporation to permeabilize cells so that nucleic acid molecules (DNA, siRNA) or other membrane-impermeable macromolecules present in the cell media can enter the cells. FIG. 4.*a* illustrates a typical cell transfection device, which consists of three components, one cell culture plate (1) as previously described, two electrode-containing plates (2, 3) placed on each side of the cell culture plate, which are used to generate adequate electrical potentials across the cells residing on porous membrane to induce electroporation. The electrode-containing plates have electrical connections (4) through which the electrodes can be accessed by outside electronics. Typically a transfection device contains an array of individual units (FIG. 4b) (a 24×16 array of transfection units are shown in FIG. 4a), cells residing in each units can be transfected separately.

In a typical process, cells (5) are first grown on the porous membrane (6) inside each cell culture unit (7), as shown in FIG. 4b, followed by introducing foreign substances (8), such as DNA, siRNA, protein, etc., to one of the two chambers (9,10) that are filled with electrical conductive media. Proper differential electrical potential is created between the two electrodes (11,12) to electroporate the cells without inducing cell damage due to irreversible membrane breakdown. Foreign substances then can enter the electroporated cells either by passive diffusion, or electrophoresis in the case of molecules with net charges, or both.

Electroporation Electrode Design

The electrode plate contains an array of electrodes used to apply electrical field to individual cell culture units. FIG. 4b shows use of probe electrodes (11,12) that have smaller size than the openings of the chambers (9,10) of the cell culture unit. The probe electrodes can be positioned close to cells so that low voltage (0.5V to 10V) can be applied to electroporate the cells. The drawback of using probe electrodes is that since the size of the electrodes are smaller than the size of the porous membrane, only the cells directly underneath the electrodes are electroporated. In addition, construction of a high-density probe electrode array can be expensive.

Figure 5:
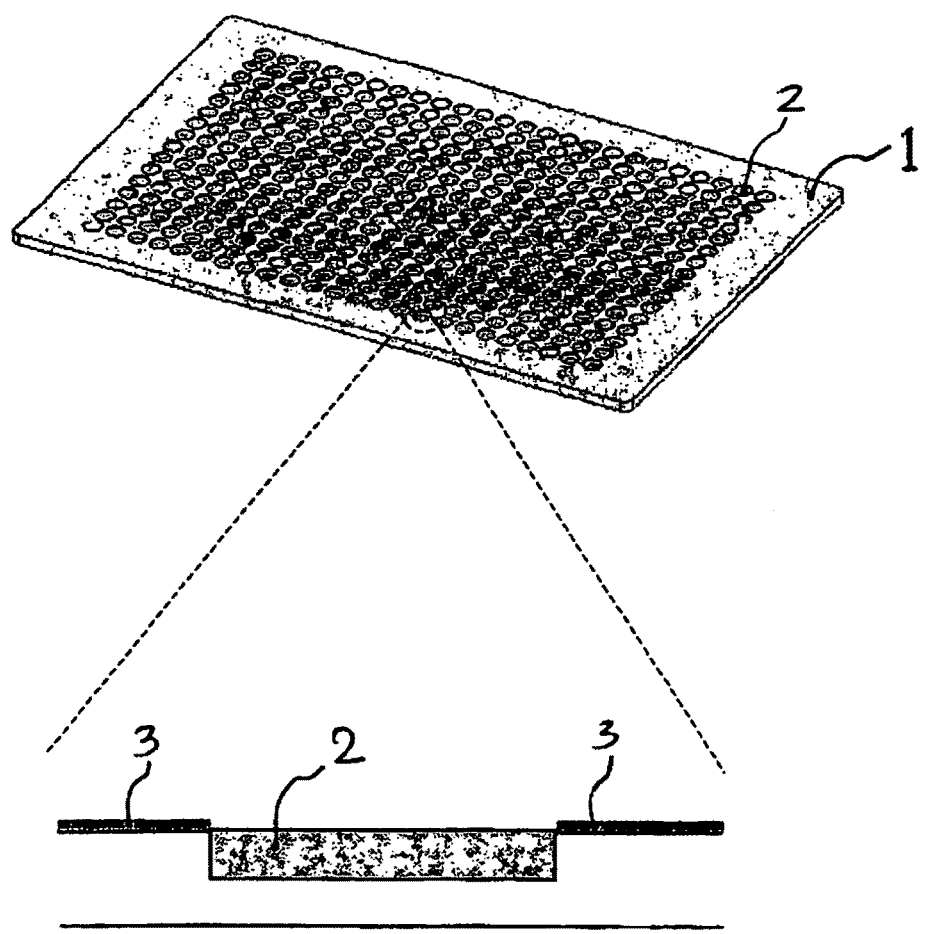
FIG. 5 is a schematic view of a plate containing an array of electrode pads.

FIG. 5 illustrates a electrode plate (1) containing an array of pad electrodes (2) that can be made at high density using techniques such as print circuit board techniques, at relatively low cost. The surfaces of the electrodes are rendered to be hydrophilic, and their surrounding areas (3) are rendered to be hydrophobic, for the purpose to be discussed below. The electrode pads are made of electrical conductive materials, including but not limited to, thin film metal, conductive composite materials, conductive gel or paste, or a combination to meet specific needs.

Establish Electrical Contact Via Liquid Droplets

In constructing high-throughput electroporation mediated cell transfection device, one of the major challenges is to implement high-density transfection units at reasonable cost without electrical cross talking and biochemical contamination among individual units. A method is hereby described to overcome this challenge by using a unique "aqueous contact" approach.

Figure 6A:
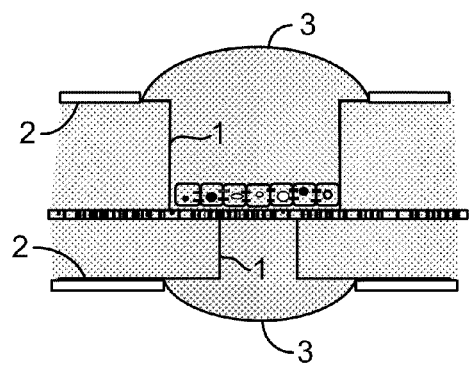
FIG. 6 is three schematic illustrations of establishing electrical connections via electrical conductive liquid droplets.
Figure 6B:
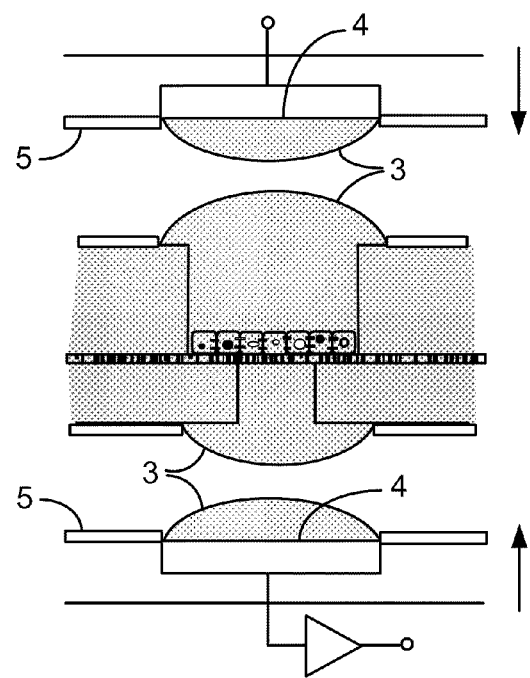
Figure 6C:
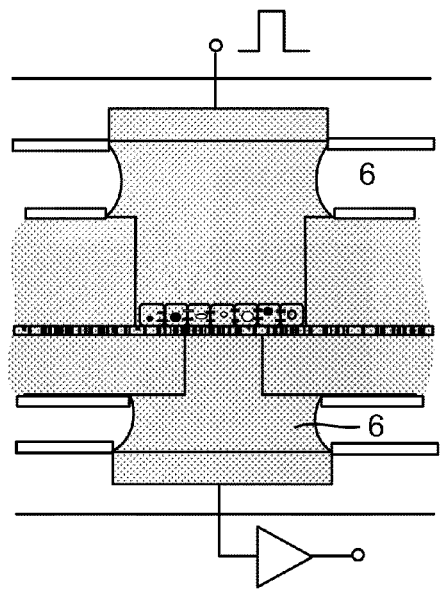

FIG. 6 illustrates the method for establishing electrical connections through convex droplets of electrical conductive media. Similarly as to the electrode plate, the cell culture plate is also treated to render surfaces (1) of inner walls of the cell culture chambers hydrophilic, and the rest of the surfaces (2) hydrophobic. With such treatment, when adequate amount of conductive liquid is added into the chambers of each cell culture unit (FIG. 6a), convex aqueous droplets (3) can be formed due to surface tension force. Furthermore, the droplets are confined to the openings of each individual unit because of the hydrophobic coating around the openings that prevent the droplets from spreading, thus eliminating cross-contamination among individual units. Using the same approach, aqueous droplets (3) are also formed atop of each electrode pad that has a hydrophilic surface (4), similarly, hydrophobic coating (5) around electrode pads is used to confine movement of droplets as previously discussed. After forming aqueous droplets (FIG. 6b), the electrode plates and the cell culture plates are brought close to let the droplets in contact and form stable aqueous plugs (6), which again are retained and contained due to surface tension force (FIG. 6c). Because both cell growth and electroporation media are electrically conductive, the confined aqueous plugs form electrical connections between each pair of corresponding electrodes without electrical cross talking and biochemical contamination. Using this approach, it is feasible to build high-density electroporation array, for example to comfort to 384-well or 1536-well industry standard high-throughput footprints.

Introduction of Nucleic Acid Molecules

In electroporation mediated cell transfection, nucleic acid molecules are usually mixed in electroporation solution and then added to cell media by manually pipetting or through use of automated liquid dispensing apparatus. This traditional approach adds additional time for sample preparation and liquid handling, which could be significant in high-throughput scenario.

To circumvent this step, nucleic acid molecules can be introduced to cell transfection device before cells are plated. In the case that pad electrodes are used, DNA or RNA molecules can be pre-deposited to each individual electrode (1) on one of the electrode-array plates (2) (FIG. 7a), then let the solution dry to leave the nucleic acid molecules (3) on the electrode (FIG. 7b). This step can be realized using commercially available microarray spotters that are capable of depositing different or the same DNA and RNA molecules in high-density and high-throughput. The nucleic acid molecule coated plate can be stored for extended period of time for later use. When cells are ready for transfection, electroporation media will be added to each electrodes as previously described, then the nucleic acid molecules attached to the electrode surface are released into the droplet (4) and brought to in contact with cells when aqueous contacts are formed (FIG. 7c). This approach also provides flexibility on where to load transfection reagents to the cells grown on one side of porous membrane, whether from the apical side (the side of cells in full contact with media) or the basal side (the side of cells in contact with porous membrane surface), by simply flipping the position (top or bottom) of the electrode-array plate that has DNA/RNA on it. This can be very useful when transfecting certain types of polarizable cells, which when form a polarized monolayer, exhibit different DNA/RNA uptake behaviors between the basal and apical sides of the monolayer. This method can also be used to introduce other molecules such as protein, peptide, etc.

Figure 8B:
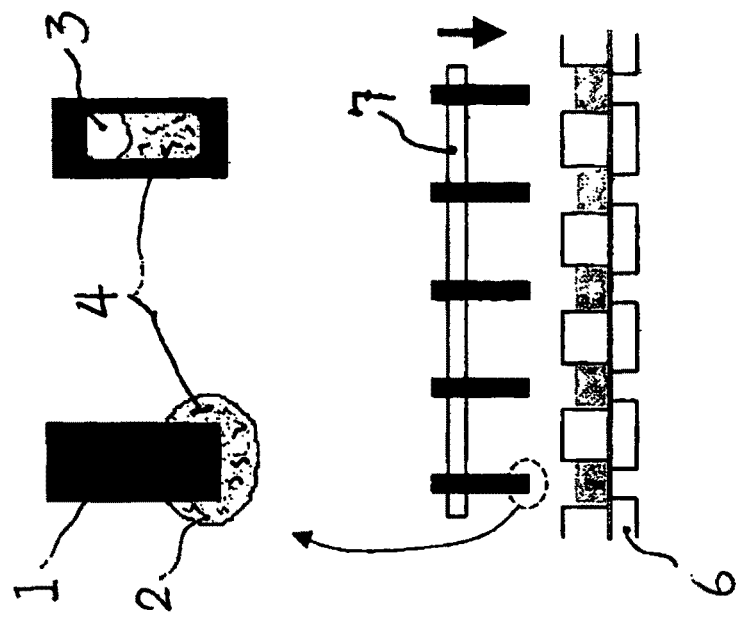
FIG. 8 is two schematic illustrations of parallel reagent dispensing through probe electrodes.
Figure 8A:
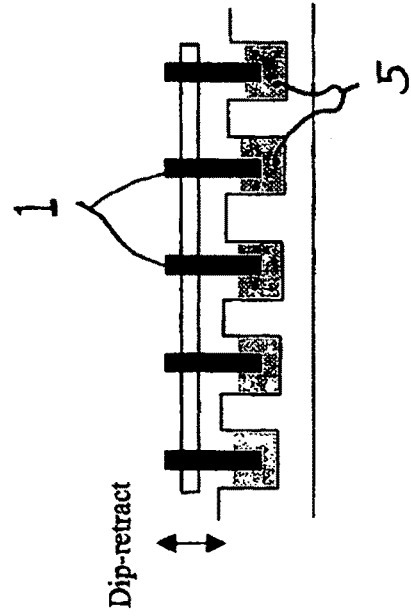

In the case that probe electrodes are used, the electrode probes can also be used to load transfection reagents such as nucleic acid molecules, as shown in FIG. 8. To achieve this purpose, one can treat the surface of the electrode probes (1) such that liquid droplets (2) can be formed at the tips of the probe electrodes due to surface tension force. Alternatively, one can cut a groove (3) near the tip of a probe electrode, and the groove can serve as a reservoir for solutions containing foreign substances such as nucleic acid molecules (4). To load foreign molecules to the probe electrodes, the probes (1) are firstly immersed in wells (5) that contain the same or different DNA solutions. After retracting the probes, small amount of reagent solution will remain on each probe, which can then be introduced to cells when the probes are immersed in cell culture devices (6). To speed up mixing of reagent in the cell culture/transfection media inside cell culture devices, small displacement vibration can be applied to the probes or the plate (7) that hold the probes. This vibration can also be applied during electroporation to reduce the possibility of aggregation of electrochemical products (such as gases) on the surface of the electrodes, which could deteriorate the surface electrochemical properties of the electrodes.

Electrode Connection and Application of Electrical Pulses

Figure 9:
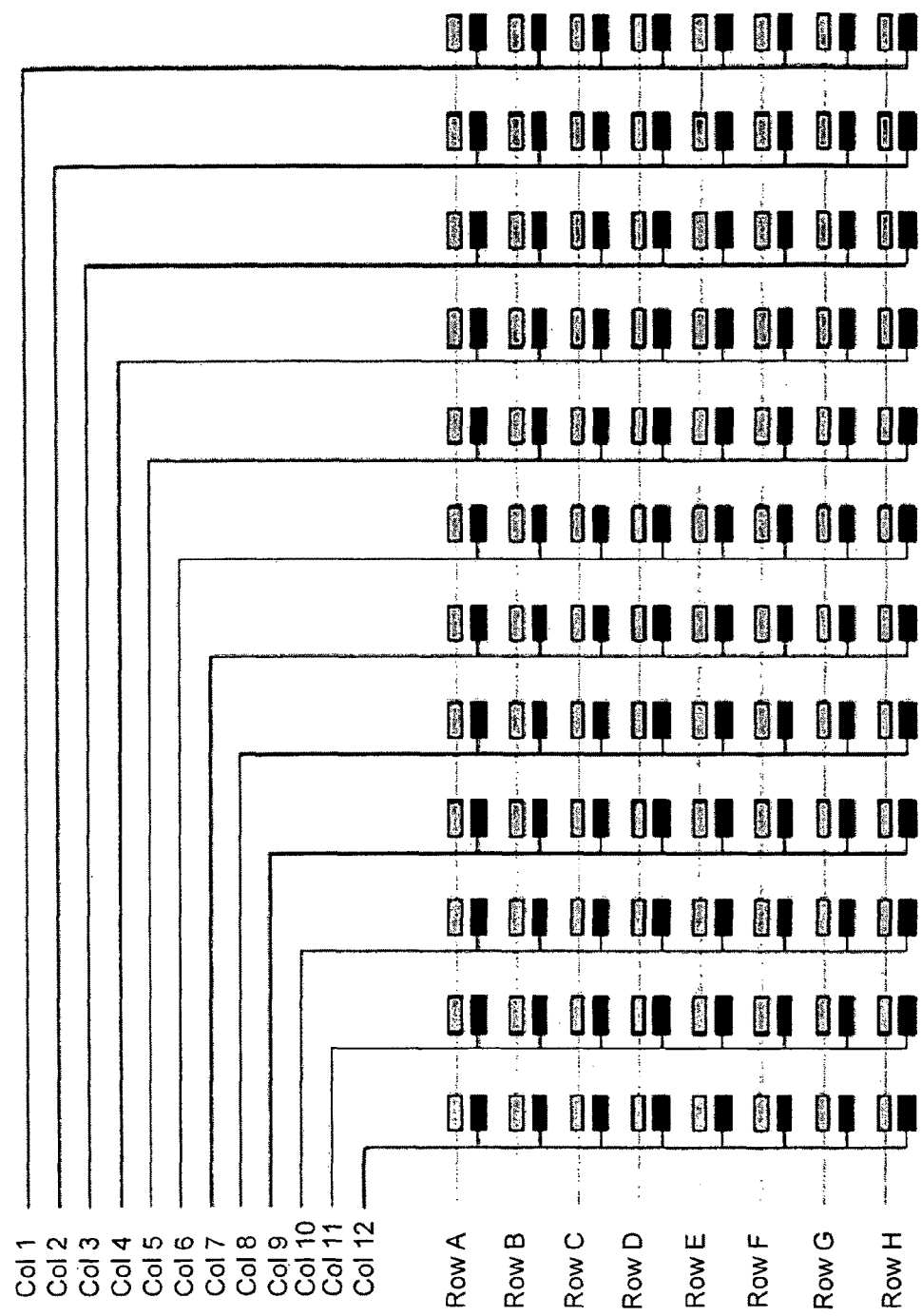
FIG. 9 is a schematic illustration of a means to connect electrodes by row and column.

In the case that a cell transfection device contains an array of individual cell transfection units, it is required to be able to electrically activate every pair of electrodes that causes electroporation of the cells in the corresponding unit, in order to optimize electroporation for cells in that unit. Our device is designed to meet this requirement with minimal requirements of wiring, which could be difficult and costly to implement in high-throughput devices. To achieve this, the electrodes on the two electrode-array plates are connected by row and column respectively. FIG. 9 illustrates electrical connections for a 96-unit in 8 (row)×12 (column) format. During electroporation process, only one row (i) of electrodes on one electrode plate is activated, similarly, only one column (j) of electrodes on the other electrode plate is simultaneously activated, which result in only activating the transfection unit that is in both row i and column j ($Unit_{i,j}$). By repeatedly activating the rest row and column of electrodes on the two plates, the entire array of units can be individually activated. Using this configuration, only 20 connections (8 rows and 12 columns) are required to be able to address every unit. For 384-well plate format that has 16 rows and 24 columns of units, only 40 connections are needed in order to activate electroporation on each individual unit, comparing to 798 (2 times of 384) wires if each electrodes are individually wired and connected to outside electronics.

Electroporation Optimization

Figure 10:
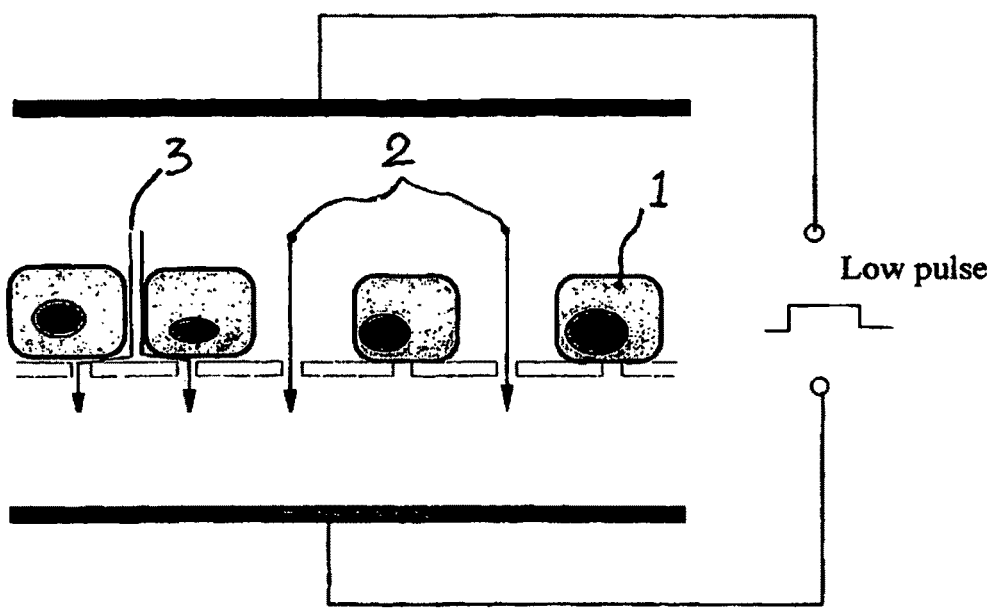
FIG. 10 is a schematic illustration of the method for measuring cell confluency

Successful electroporation depends on many parameters. In the case of using the device disclosed in the present invention, the two most influential parameters are cell type and confluent state of cell monolayer. When cells are the same, the higher confluency of the cells (means more areas of the substrate cells grow on are covered by cells), the less intense electrical pulses are needed to electroporate the cells. The confluent state of the cell monolayer can be measured electrically by applying a low amplitude electrical pulse between two electrodes (FIG. 10). Because the pulse doesn't induce electroporation in cells (1), the electrical current through normal cells is negligible. Thus, the electrical current flowing between the two electrodes comprises two component, i.e., leakage current (2) that passes through the areas of the porous membrane not covered by cells, and paracellular current (3) that flows between the gaps among cells and between cell and porous membrane substrate. The leakage current is directly determined by cell confluency since the higher the cell confluence, the less number of pores not covered by cells, thus the larger electrical currents can flow when the same electrical potential is applied between the electrodes. In most cases, the paracellular current is much smaller than the leakage currents, thus leakage current can be approximated with the electrical current flowing between the electrodes, and the state of cell confluency can be estimated. With the information on cell confluency and cell type, electrical pulses can be optimized to achieve high degree of electroporation while avoiding excessive cell damage. A computer program can be used to determine parameters (amplitude, length and shape) of electrical pulses based on theoretical calculation, experimental data, or the combination, to achieve optimal electroporation for the given type of cells in a given confluent state (measured by electrical currents under a constant measurement pulse).

Minimize Effect of Cell Growth Ununiformity

Figure 11A:
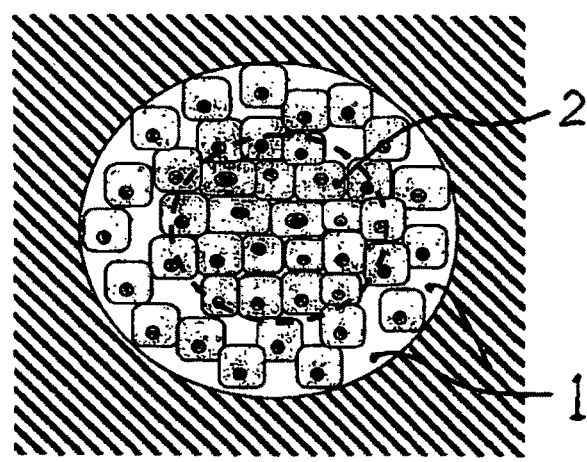
FIG. 11 is three schematic illustrations of effect of ununiformity in cell attachment on electrical currents flowing through a porous membrane with cells, and a design to overcome the effect.
Figure 11B:
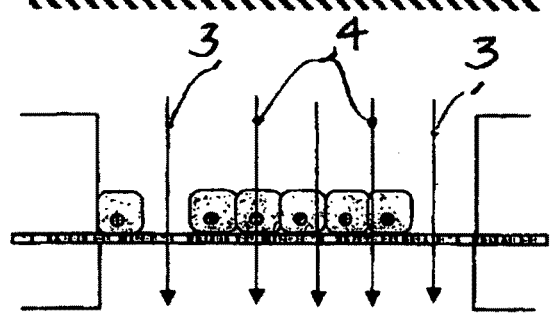

When electroporating a cell monolayer grown on top of a porous membrane using long electrical pulses, it is important that the porous membrane is effective covered by the cell monolayer, which results in maximal degree of electroporation effectiveness under the same electrical pulses. However, as illustrated in FIG. 11a, most times cells don't cover the entire substrate they grow on, particularly toward the edge of a chamber where there are always large patches of openings (1) not covered by cells, even cells reach a high degree of confluency in the central areas (2). The exposed patches of porous membrane at the edge of the chamber often cause less effectiveness in cell electroporation as they allow a substantial amount of leakage current (3) passes directly through the porous membrane (FIG. 11b), instead of through the cell monolayer as effective electroporation Current (4) that forces cell membranes to be permeabilized.

Figure 11C:
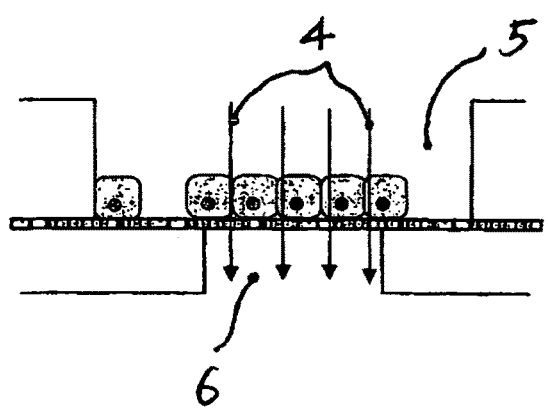

To overcome this edge effect in cell growth, one can block the pores in the edge region of the porous membrane, thus minimize leakage current that otherwise can flows through the uncovered pores. This concept can be readily realized by making the opening of the top chamber (5), in which cells are cultured, larger than that of the bottom chamber (6), as shown in FIG. 11c. By this means, electrical current can only flow through the central region of the porous membrane/cell monolayer, which is defined by the opening of the bottom chamber, thus effectively eliminating leakage current through the edge of porous membrane/cell monolayer.

Selective Cell Electroporation and Transfection

Another important benefit arising from the device described in FIG. 11c is the ability of realize electroporation, and thus transfection, in a selective fashion. Using the method and device in the present invention, a cell can be electroporated only when it is exposed to at least one unobstructed microscale pore, which permits passage of electroporation current through the cell. If there is no pore beneath the cell or the pores are blocked, the cell will not be affected by the present electrical field. Therefore, blocking pores in specific region of the porous membrane provide an effective means to achieve selective electroporation and transfection. In the device shown in FIG. 11c, the smaller chamber also defines an electroporation window in the central region of the porous membrane/cell monolayer, with cells inside the window, or cells directly on top of the bottom chamber opening, can be electroporated. The rest of the cells outside of this central window will not be electroporated and thus transfected since their underneath pores are effectively blocked by the dielectric body of the bottom chamber. The unaffected cells can serve as negative control cells, which are very useful to study side-by-side how the transfected cells differ from the unaffected ones due to incorporating of foreign molecules. To achieve selective electroporation with more sophisticated pattern, one can use techniques such as glue spotting, screening printing, etc., to precisely blocked pores at desirable areas of the porous membrane.

Cell Transfection Apparatus

Figure 12:
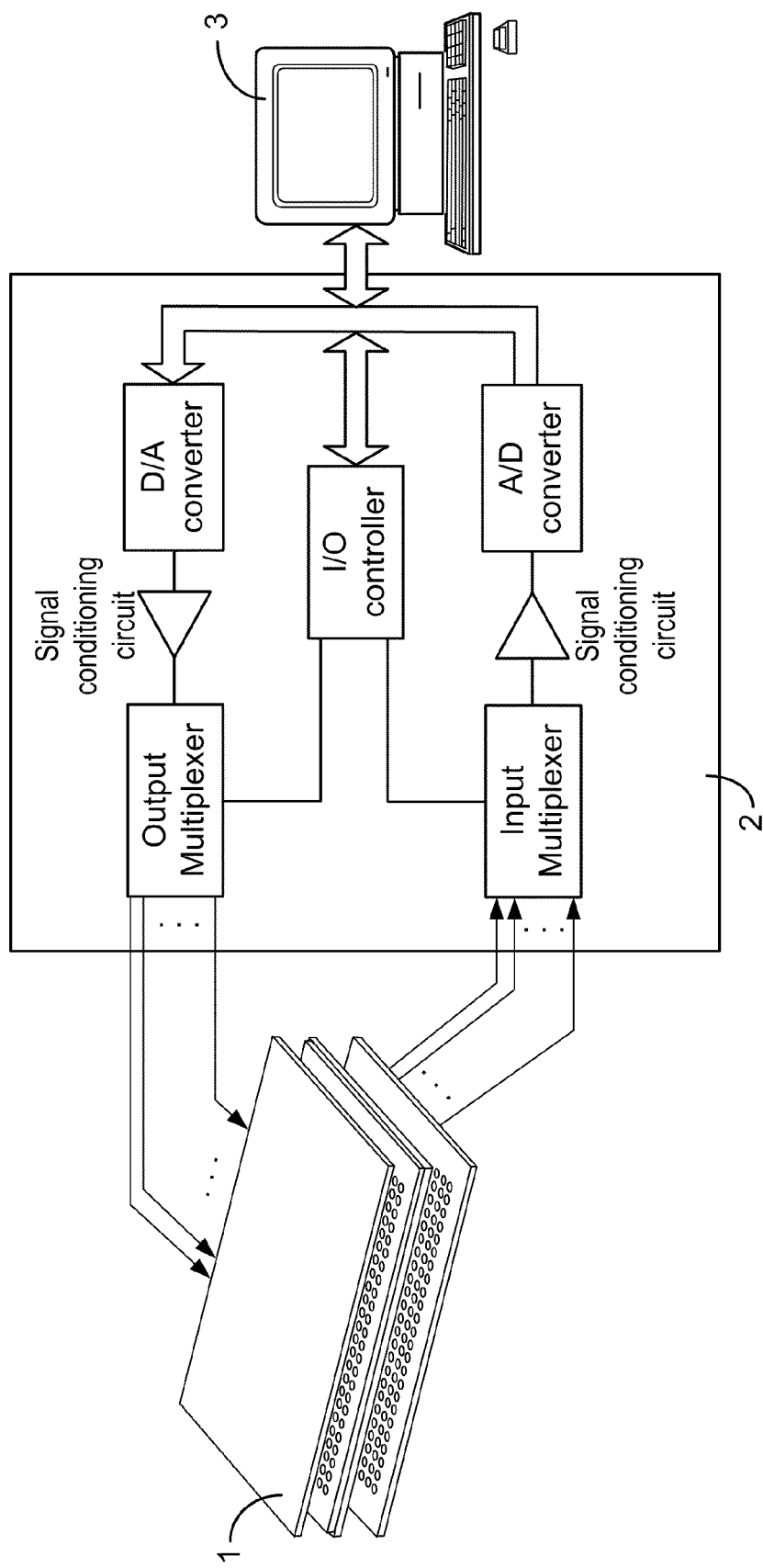
FIG. 12 is a schematic diagram of a typical cell transfection apparatus

A cell transfection apparatus (FIG. 12) typically comprises a cell transfection device as previously described (1), an electroporation control apparatus (2) and a computer (3). The computer can be either a personal computer linked with the control apparatus or a microprocessor system embedded in the apparatus. The computer determines electroporation conditions for a particular transfection unit on the cell transfection device, the information is then directed to the control apparatus that selects and drives a pair of electrodes corresponding to a particular transfection unit to achieve optimal electroporation in the cells residing in the device.

Improving Nuclear Importation of DNA Molecules

In transfecting cells with DNA molecules, the DNA molecules (mostly DNA plasmids) need to enter cell nucleus in order to be expressed. This can be a challenging issue in transfecting non-dividing cells as unlike in dividing cells foreign genes can be incorporated in the nuclei of daughter cells during mitosis, genes in the cytoplasms of non-dividing cells need to find a way to enter nuclei, otherwise they will be quickly degraded by cytoplasmic nucleases.

Figures 13A, 13B:
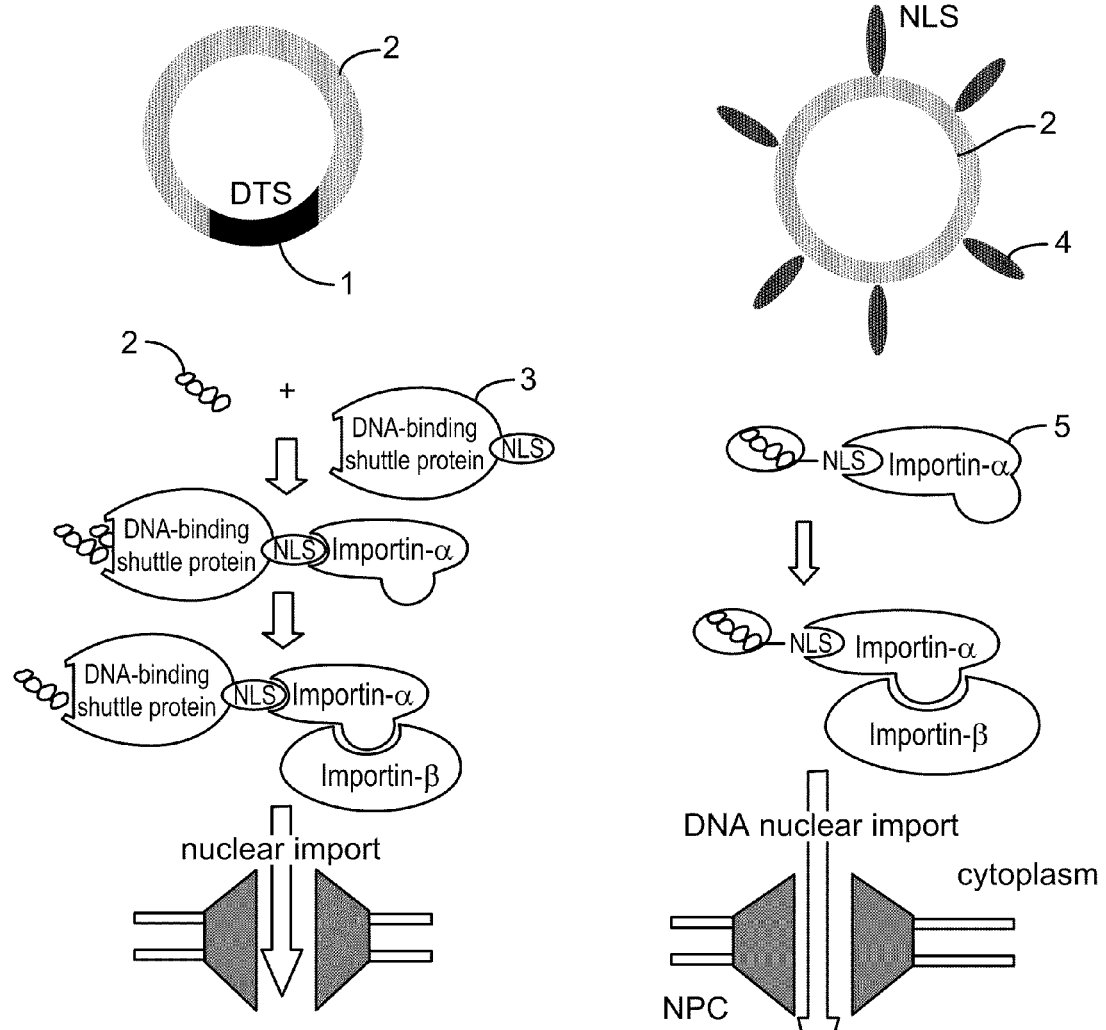
FIG. 13 is a schematic demonstration of two methods for improving delivery of DNA molecules into cell nuclei.

There are a couple of techniques to improve the efficiency of transporting DNAs from cytoplasm to nucleus, which when combined with our electroporation method can produce better gene transfection efficiency. One technique involves incorporating DNA nuclear targeting sequence (DTS) (1) in DNA plasmid vectors (2), which improves nuclear localization of the DTS-containing DNA molecules through piggybacking with DTS-binding proteins (3) that can enter cell nucleus (FIG. 13.a). Another method involves attaching nuclear localization signal (NLS) peptide (4) to DNA plasmids, the NLS peptide can directly modulate proteins (5), such as importins, that control the traffic through nuclear envelope, so that the NLS-attached DNA plasmids can enter nucleus through nuclear pore complexes (FIG. 13.b)

Auxiliary Component for Culturing Cells

The transfection method described in this invention requires cells to grow into a relatively confluent monolayer before they can be electroporated and transfected. This normally takes a couple of days. Such long culture time requires sufficient cell growth media to keep cells healthy, which is an issue in culturing cells on high-throughput plates as their wells are small in volume and liquid evaporation is a big issue at this physical scale. One approach to solve this problem to is change media from, time to time manually or using robotic media change station, a tedious and time-consuming procedure. As an alternative approach, we disclose two methods for increasing culture media accessible to cells in each cell culture unit.

Figure 14:
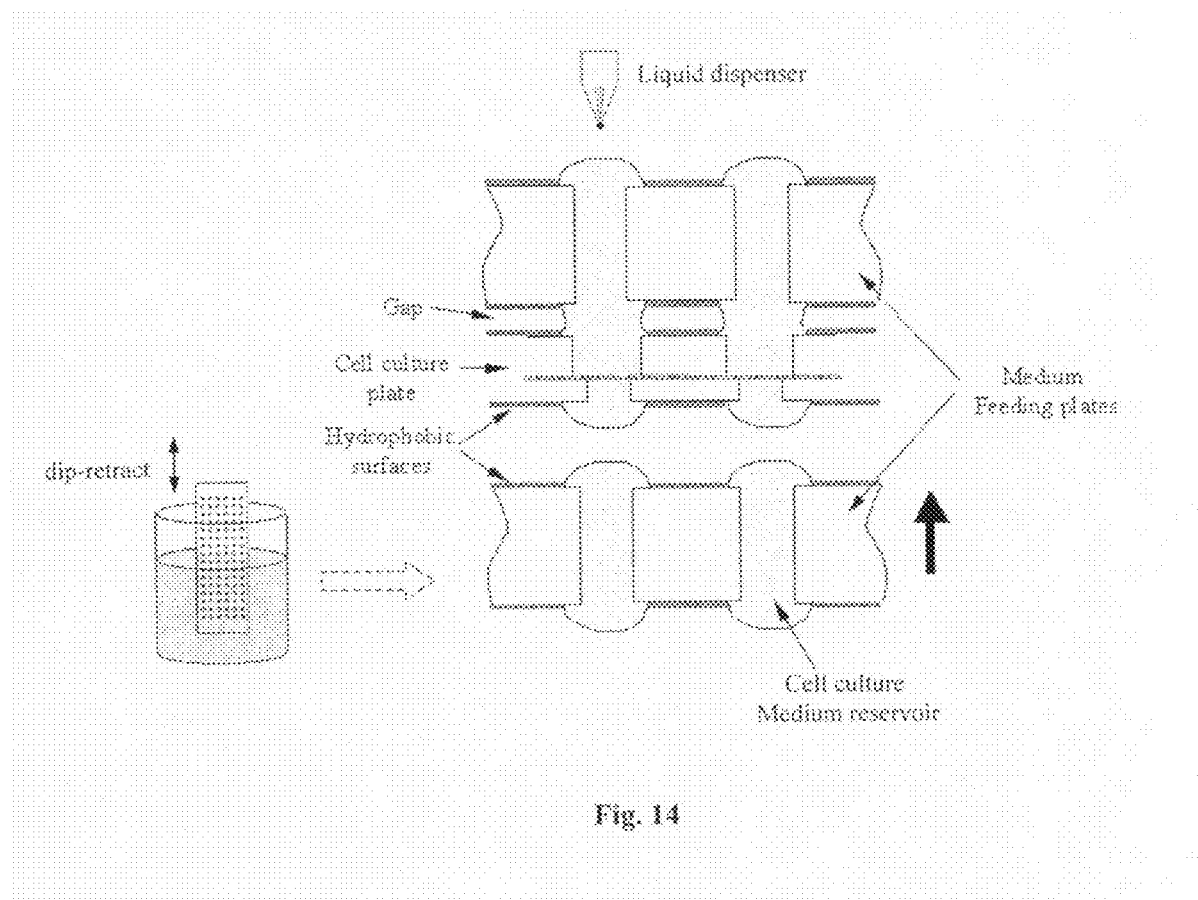
FIG. 14 is a schematic illustration of using auxiliary medium feeding plates to add more culture media to cells grown in the cell culture device in FIG. 2

FIG. 14 illustrates one approach that uses specially designed detachable cell culture medium feeding plates. The feeding plates (1) have array of liquid reservoirs that are aligned with every individual transfection unit of a cell culture plate (2) where cells reside. The thickness of the plates can range from 1 mm to 50 mm depending on how much medium each reservoir is expected to accommodate. The reservoirs' inside and the vicinity of their openings are treated to be hydrophilic (3) and the rest areas (4) are rendered to be hydrophobic so that when adequate amount of liquid added to each reservoir, convex liquid droplets (5) can form at the openings of each reservoir. Loading reservoirs with cell culture media can be done using pipetting techniques (6) (manual or automatic), or simply by immerse plates in culture media then pull them out gently (dip-and-retract) (7), each reservoir will be filled with liquid thanks to capillary effect and liquid droplets will form automatically due to surface tension force. Once the auxiliary plates are loaded with media, they are brought to a proper distance to a cell culture plate that also have convex liquid droplets formed at the openings of each individual unit, the droplets are brought into contact and merge, they become small fluidic plugs (8) connecting reservoirs with their corresponding cell transfection units where cell reside. For illustration purpose, only one feeding plate (1) is brought closely to the cell culture plate (2) to form a fluidic connection. The bottom feeding plate (2) is separated from the cell culture plate to demonstrate how the fluidic connection is formed by liquid droplets (5). Then the assembled device can be placed in cell culture incubator. As the thickness of the auxiliary medium feeding plate can be large, culture media reservoirs can hold enough media to feed cells for extended culture time. When cells are ready for electroporation, the cell cell culture plate is then separated from the cell culture plates for downstream operations.

Figure 15A:
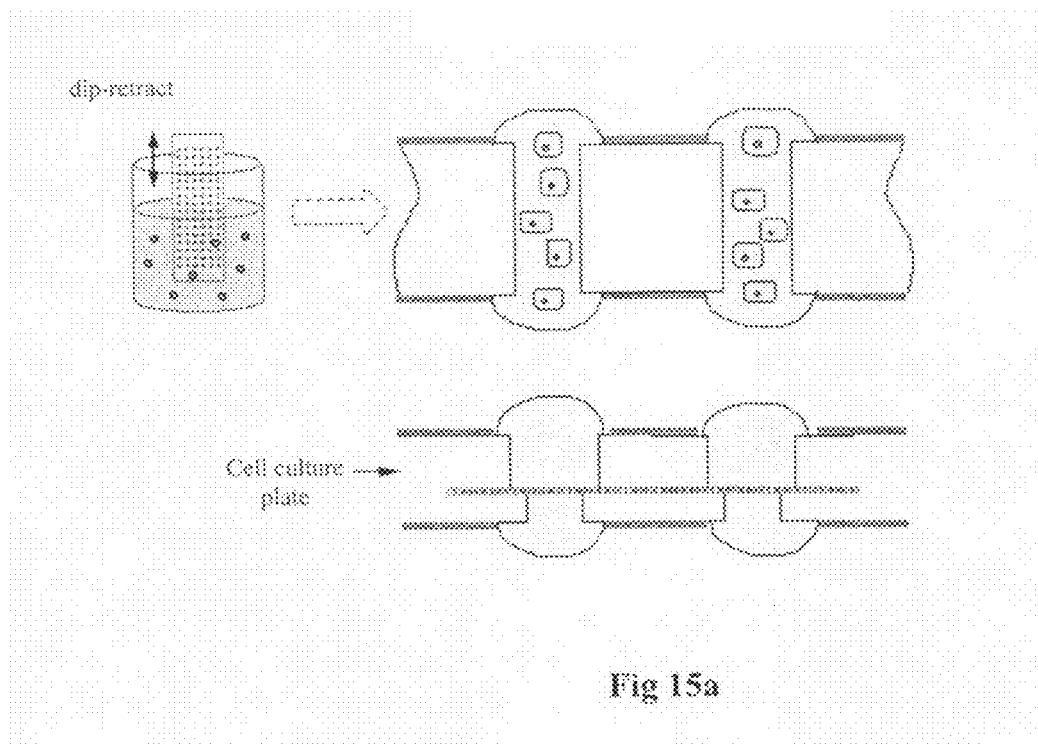
FIG. 15 is two schematic illustrations of a method for parallel cell plating
Figure 15B:
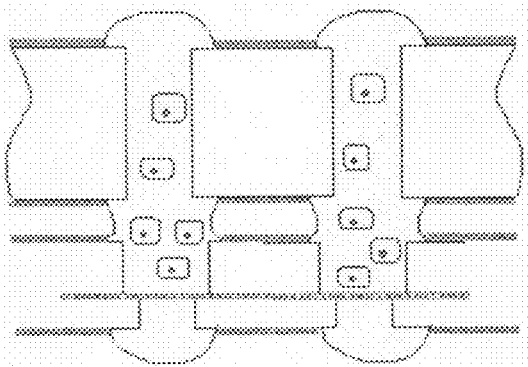

It should be noted that the medium feeding plate can also be used for parallel cell loading, which is demonstrated in FIG. 15. Using the same "dip-and-retract" approach as illustrated in FIG. 15a, a feeding plate (1) is submerged in a solution (3) containing biological cells (4), then gently retracted. Due to surface treatment of the feeding plate previously described, cell-containing solution fills in each opening of the feeding plates and forms convex liquid droplets (5) at the exits of the openings due to surface tension forces. A cell culture plate (2) is also loaded with proper cell culture solution in each transfection units using methods described previously. Convex liquid droplets (6) are also formed at the exits of each transfection unit due to surface tension forces. When the feeding plate and the cell culture plate are brought close (FIG. 15b), the liquid droplets (5 and 6) eventually merge to form a liquid connection (7), through which cells (4) in each opening of the feeding plate can travel to the corresponding transfection unit, thus completes cell loading process.

Figure 16A:
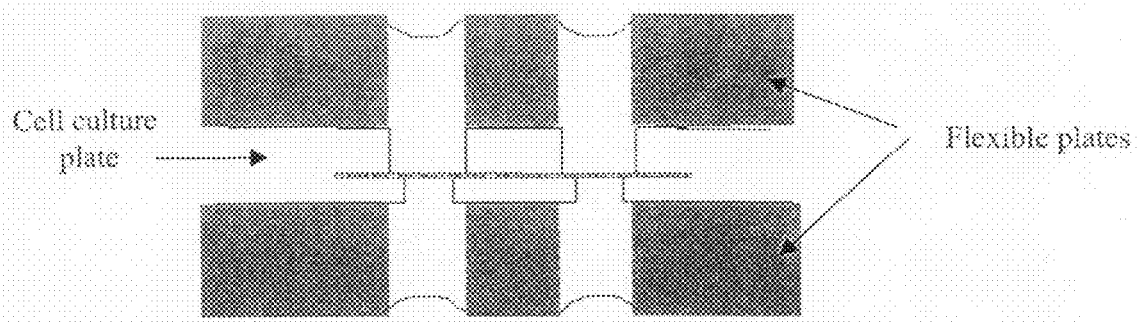
FIG. 16 is two schematic illustrations of using flexible auxiliary medium feeding plate to add more culture media
Figure 16B:
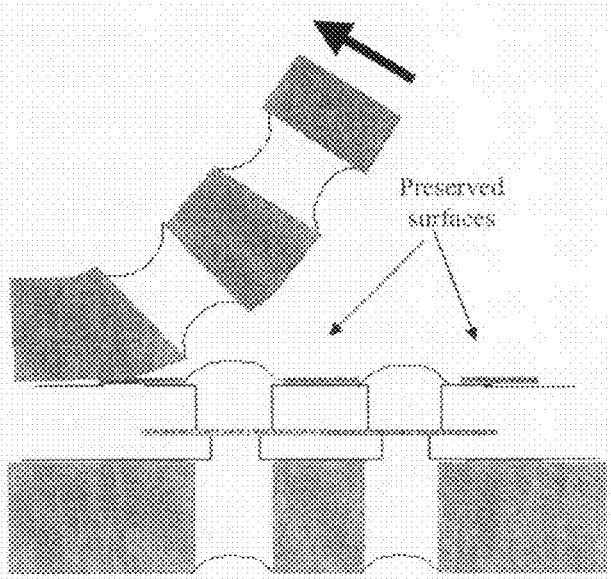

FIG. 16 illustrates another approach that uses disposable flexible plates to increase cell culture volume. In this case, two flexible plates (1) made of elastic inert materials (such as PDMS silicone rubber) are directly attached to a cell culture plate on both sides through temporary bonding (FIG. 16a). The inner surfaces (7) of each opening of the flexible plate are treated to be hydrophilic, and the rest surfaces (8) are hydrophobic. The two attached plates allow adding more culture media (3) to feed the cells in each transfection unit of a cell culture plate (2). In some special cases, cells might need to be culture for several weeks to reach a desirable biological state before they are transfected. For such expended long time of culturing, the entire assembly (cell cell culture plate and disposable plates) can be immersed in a cell culture container, after cells attach to the porous membrane of each transfection unit (normally takes 4-6 hours after cells are introduced to the membrane surface). The attached plates also serve as protection layers to protect the hydrophobic-treated surfaces (6) of the cell culture plate from being exposed to and effected by cell culture media. When the cells are ready for electroporation and transfection, the flexible auxiliary plates (1) are peeled off from the cell culture plate (2) (for illustration purposes, only the top flexible plate is peeled off in FIG. 16b). Excessive cell culture solution is also automatically removed as it is retained inside the openings of the flexible plate due to surface tension force. The rest of the cell culture solution remains in each transfection units of the cell culture plate, with convex droplets formed at the exits of the transfection units due to the protected hydrophobic surfaces (6), making them ready for downstream downstream transfection procedures as described previously.

EXPERIMENTAL RESULTS

Cell Culture

Various types of cells, including engineered cell lines (such as HepG2, MDCK, HEK293) and primary cells (such as HMEC, HUVEC, PrEC), are tested using the described device. To culture cells in the cell culture device, cells are firstly trypsinized and resuspended in culture medium, followed by adding cells to a cell culture unit at seeding density between 50,000 to 500,000 cells per $cm^2$ of porous membrane. Cell culture device is then placed inside an incubator at 37 C with 5% $CO_2$ for one or two days before they are electroporated and transfected. This practice typically leads to formation of a >80% confluent cell monolayer on the porous membrane.

Electroporation Study

Figure 17:
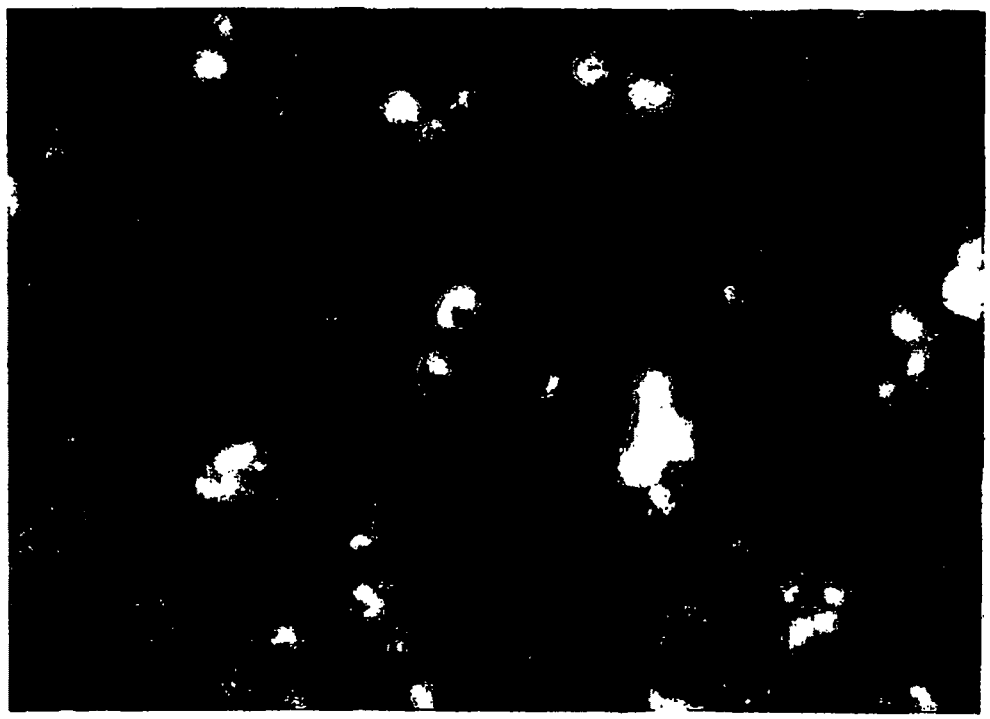
FIG. 17 is an image of MDCK cells stained by YOYO-1 fluorescent dye

Electrical pulses with width between 100 msec to 5 sec are applied to a pair of electrodes for cell electroporation. Depending on cell type and confluence of cell monolayer, amplitude of electrical pulses ranges from IV to 3V for optimal electroporation of different types of cells. A nucleic acid staining fluorescent dye, YOYO-1 (Invitrogen), is used to assess the effective of electroporation. YOYO-1 molecules can not enter normal cells since they are membrane impermeant. When cells are electroporated, YOYO-1 molecules can enter the cells through their permeabilized membrane, and bind to cellular DNA and RNA molecules. Thus, the YOYO-1 containing electroporated cells can be readily identified as they appear to be green under proper UV excitation. FIG. 17 shows MDCK cells that are electroporated in 1 uM YOYO-1 solution (in PBS) by a 2.5V/1 second square pulse. To facilitate fluorescent observation, MDCK cells are detached from porous membrane and loaded on a glass slide. In the figure, bright cells indicates successful incorporation of membrane impermeant YOYO-1 molecules due to electroporation. It can be seen >90% of the cells appear to be bright/white, indicating >90% of the cells are effectively electroporated under that particular condition. Similar results have also been achieved with other cells, including both cell lines and primary cells, such as HEK293, HUVEC, PrEC, etc.

Transfection of DNA

Figure 18A:
FIG. 18 is two images showing effective DNA transfection in two primary cell lines
Figure 18B:

FIG. 18 demonstrates the capability of the cell transfection device in transfection of cells with DNA plasmids. In the experiment, DNA plasmids solution (10-50 ug/mL) is added either in the apical or basal side of a cell monolayer, then cells are electroporated with square electrical pulses between 1.5V-3V. Expression of the DNA plasmids is observed four to 24 hours after electroporation. It should be noted that using our transfection method, expression of DNA plasmids is evident as early as three hours after transfection, which is significantly shorter than other transfection methods (normally 24 hours). This rapid expression of DNA molecules implies effective nuclear uptake of the DNA plasmids using our method. FIG. 18a shows successful GFP (Green Fluorescent Protein) expression in a confluent monolayer of PrEC cells (human prostate epithelial cells). More than 70% of the cells are successfully transfected and express GFP, which appear bright in the image. FIG. 18b shows GFP expression in a confluent monolayer of HMEC cells (human mammary epithelial cells). More than 40% of the cells are successfully transfected (bright cells in the picture). It should be noted that both PrEC and HMEC are primary cells, which are typically very resistant to existing transfection methods, such as lipofection. Being able to transfect primary cells in high-throughput fashion grants our technology clear advantages over the existing ones.

Transfection of siRNA

Figure 19:
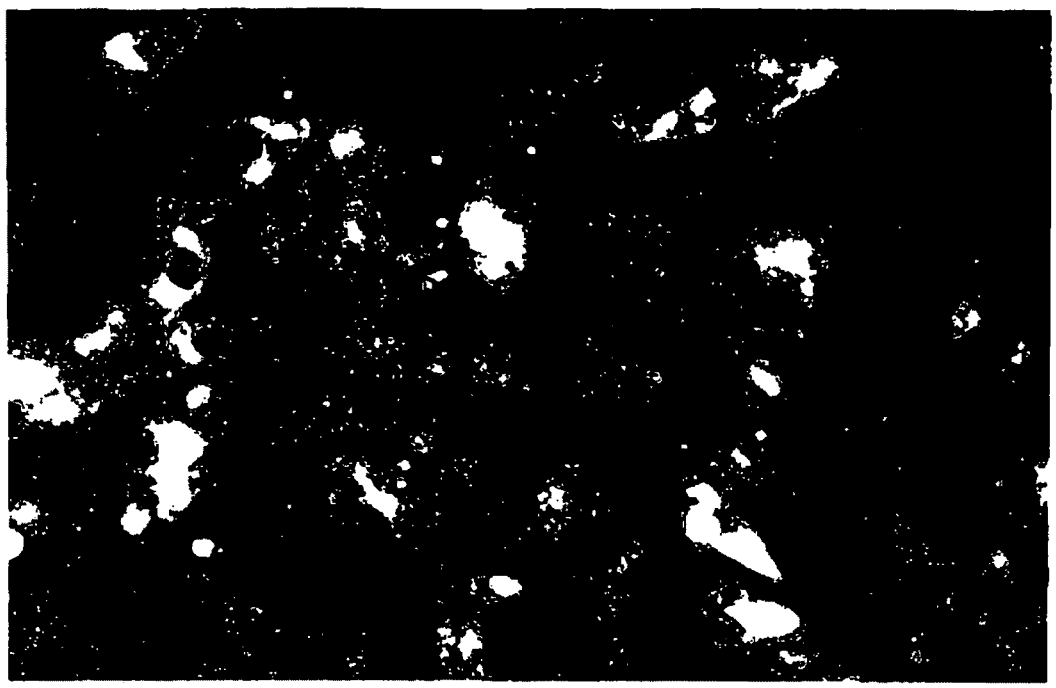
FIG. 19 is a image of PrEC cells transfected with labeled siRNA
Figure 20A:
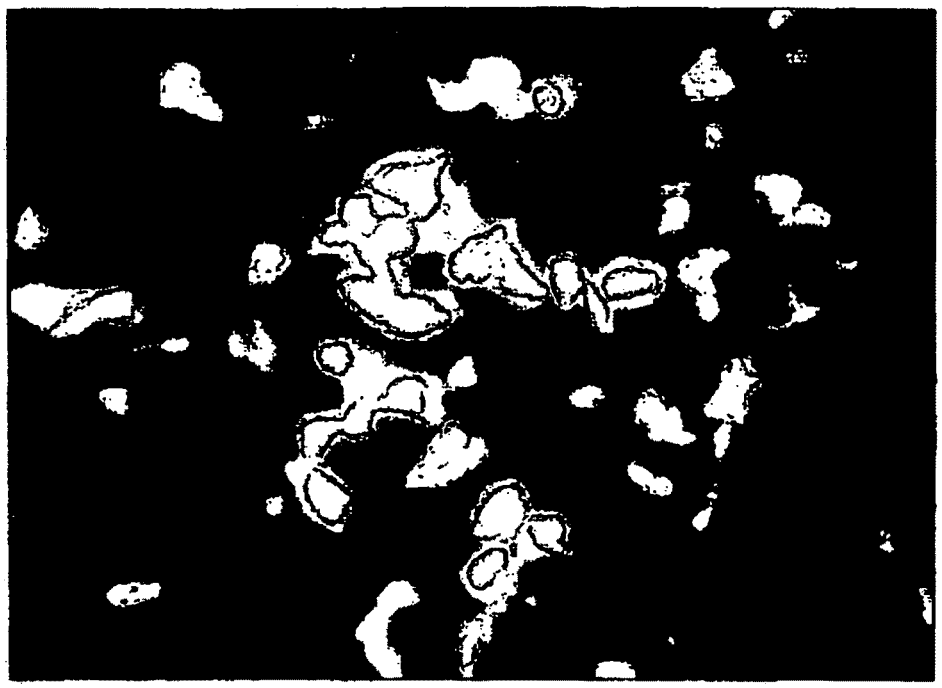
FIG. 20 is two images showing effective knockdown of GFP in PrEC cells by effective siRNA transfection
Figure 20B:

To demonstrate our device's capability of transfecting cells with siRNA, we added 20 nM fluorescence labeled siRNA (Alexa Fluor 488-siRNA from Invitrogen) to PrEC cells, then electroporated the cells using similar protocols described above. FIG. 19 is an image showing effective introduction of the siRNA molecules into more than 60% of cells (bright cells). To further demonstrate our capability, we first transfected PrEC cells with GFP vectors. FIG. 20a shows many bright cells indicating high level GFP expression. Then we further transfected the same cells with 10 nM anti-GFP siRNA (Invitrogen), which can knock down GFP expression once they are delivered into cells. FIG. 20b shows an image of the same cells twelve hours after siRNA transfection. It is obvious that cells appear much dimmer than before (FIG. 20a), which indicated successful known-down of GFP in the cells by anti-GFP siRNA molecules delivered using our device.

Selective Electroporation and Transfection

To demonstrate the capability of performing selective electroporation, we used a UV curable transparent paste to block the edge region of the porous membrane in a cell transfection device. Cells are cultured on the other side of the porous membrane as previously described. Then the cells are electroporated in presence of a red nucleic acid stain, propidium iodine (PI), using similar conditions above. Then cells are inspected using fluorescent microscopy. FIG. 20 shows a fluorescent image of MDCK cells after electroporation. The white dash line outlines the boundary of the cured transparent paste, which blocked the left side of the porous membrane. MDCK cells formed a nice confluent monolayer span across the entire porous membrane (image not shown). While as shown by the images, only the cells on the unblocked part of the porous membrane (right side of the dash line) are successfully electroporated (indicated by PI uptake that make the cells appear to be bright in the image). The cells on the blocked area (left side) were virtually unaffected since no PI uptake is detected (cells are dark and not visible in the image).

Figure 21A:
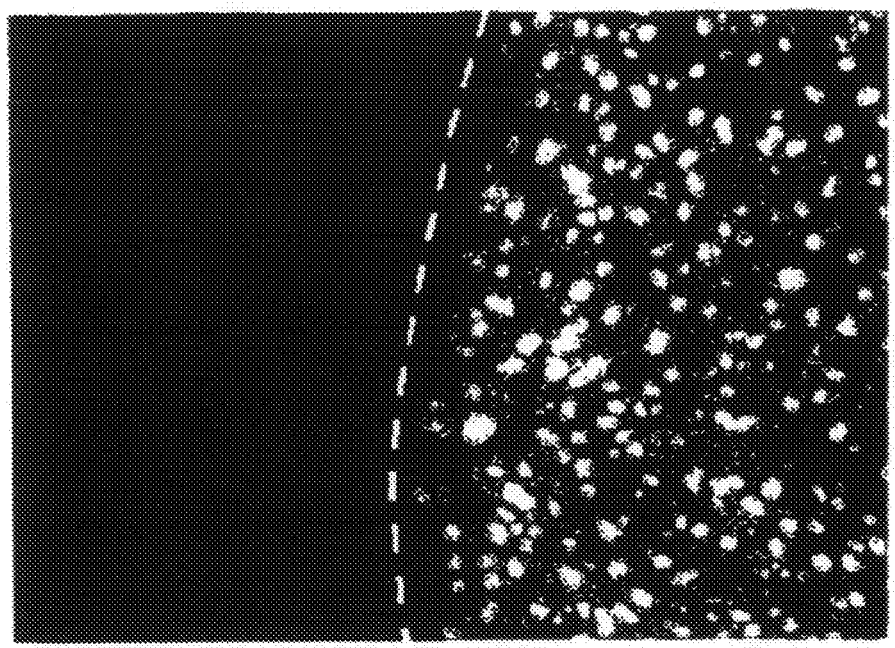
FIG. 21 is two images showing selective electroporation and transfection in MDCK and PrEC cells
Figure 21B:
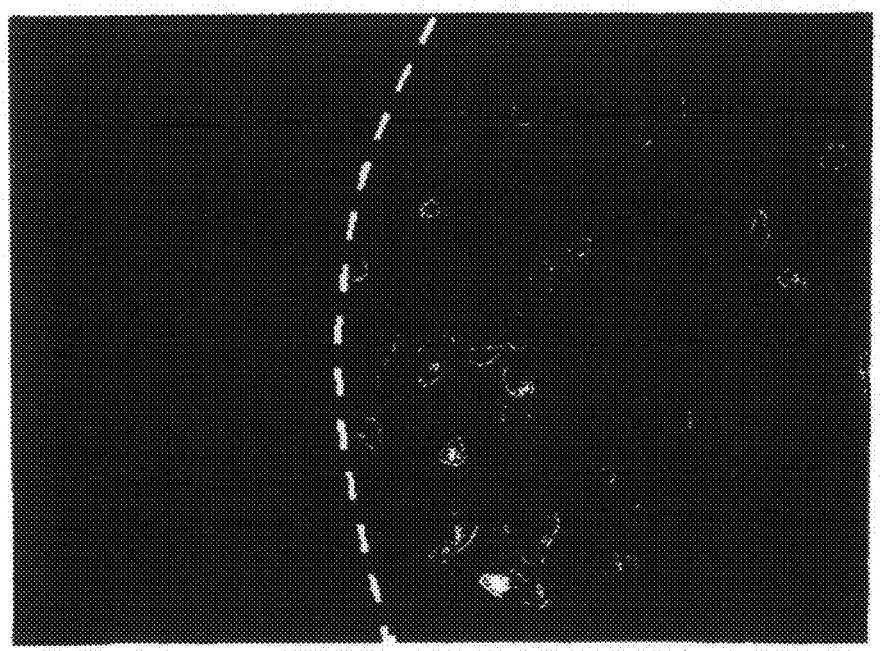

Using the same method, we also performed selective cell transfection successfully in PrEC cells. GFP plasmids are used to indicate successful cell transfection. FIG. 21 shows a fluorescent image of the cells. Similarly, a white dash line outlines the boundary between porous membranes with blocked and open pores. Again, the experiment shows that only the cells on top of the porous membrane with unobstructed pores express GFP due to successful transfection (bright cells at the right side of the dashline). The rest of the same cells under same electroporation conditions are virtually not affected. Both experiments validate that selective electroporation and thus transfection can be achieved in our devices by blocking part of the porous membrane.

Methods of Use

The high-throughput cell transfection method disclosed in this invention can enable many cell-based assays for both fundamental research (such as functional genomics, cancer research) and therapeutic development (such as target ID/validation, compound screen and in vitro testing).

Besides the general usage of the high-throughput transfection device and apparatus, we also disclose hereafter novel methods of using transient transfected cells for evaluation and prediction of drug compounds' pharmaceutical and therapeutic properties. It should be noted that the methods to be disclosed can be realized by the aforementioned high-throughput cell transfection method and apparatus, however, they are not necessarily limited to any particular transfection methods or apparatuses.

Method for Transcription Factor Activity Profiling

Transcription factors (TFs) are a family of regulatory proteins of critical importance as they control when genes are switched on or off. Knowing the functional activities of transcription factors not only offer information on which genes will be transcripted (switched on), but also can give insights on which signaling pathways are affected by stimuli (such as drugs, toxins, environmental stress, etc.) since activation of transcription factors is normally the last step of signaling pathways. Furthermore, since it is the activation of particular set of transcription factors that turned on a particular set of genes that drive pathophysiological and physiological responses to external stimuli in human body, it is feasible to predict how human body responses to a particular stimulus (drug, toxin, environmental stress, molecular defect, etc.) by analyzing changes in functional activities of the entire family of transcription factors, or a subset of pertinent transcription factors.

The functional activity of a particular TF can be analyzed by transfecting cells with a TF reporter vector that contains a cis-acting DNA response element upstream of the reporter gene. The reporter gene can encode any reporters such as luciferase, GFP, beta-lactamase, etc. The cis-reacting response element contains multiple repeats of a specific TF binding element. When the vector is transfected in cells, activation of the specific transcription factor will result in binding of the TF and the cis-acting element that recognize the TF, which cause transcription and expression of the reporter gene, producing a detectable signal as the result of activation of that particular TF.

To analyze the activities of a group of interested TFs in cells, it is necessary to construct a library of TF reporter vectors, each reporter vector contains cis-acting element that is recognized by a corresponding TF. Then one can use the transfection device previously described, or use any other applicable methods, to transfect a number of the same cell samples with the TF reporter vectors, one vector for each sample. Each transfected cell sample is used to elucidate the functional activity of one TF, collectively, one can profile the activities of a large number of TFs in a particular type of cells (primary cells or engineered cell lines).

When the cells are subject to a stimulus, comparing the functional activity profiles of a particular set of TFs in cells before and after stimulation can reveal which TFs' activities are affected by the stimulus (drug, toxin, stress, radiation, molecular change, etc.) This can be particularly useful to evaluate the effects of the stimulus and to understand the underlying mechanisms that cause the actions (Mechanism-Of-Action).

It should be noted that in order to compare TFs' functional activities in the same cells before and after stimulation, the reporter used must permit analysis of the reporter activity in live cells. Such reporter can be GFP, renilla luciferase, beta-lactamase, etc. If the reporter chosen requires lysing cells (e.g., firefly luciferase), two sets of experiments need to be carried out, with one set of transfected cells not being treated with stimulus to serve as negative controls/references, the other set of transfected cells to be treated with stimulus in order to obtain the corresponding TF activity profile. The changes in TF activities can be extrapolated by comparing the two profiles obtained from different sets of cells.

To recapitulate, the method for profiling the changes in functional activities of a set of transcription factors caused by a stimulus comprise typically the following steps,
  a. Transfecting at least one type of model cells (primary cells or engineered cell lines) with a library (>2) of TF reporter vectors, with one population of cells transfected with one TF reporter vector that can recognize functional activity of a specific TF inside the cells.
  b. Measure reporter activities through fluorescence, luminescence or any appropriate techniques, in each population of cells, to evaluate the functional activity of the specific TF corresponding to the IF reporter vector being transfected in this particular population of cells.
  c. Construct a profile of the functional activities of all TFs of interests
  d. If the reporter system used allows live cell analysis, subject the previous cells to a specific stimulus, repeat step a-c, to obtain a second profile of TF activities in the same cells after stimulation. If the reporter used doesn't allow live cell analysis, start with a new batch of same model cells, subject the cells to the stimulus, then go through step i-iii to obtain a second profile of TF activities in the model cells that underwent stimulation.
  e. Compare the first and second profiles to identify changes in functional activities of the TFs the type(s) of model cells caused by the stimulus Target Evaluation and Biomarker Discovery Using TF Activity Profiling Modern drugs often modulate target proteins that play important roles in pathological pathways. Direct or indirect modulation of the targets often result in changes in activities of many expected and unexpected transfection factors because of cross-talking among signaling pathways. The aforementioned TF activity profiling method can be used to evaluate therapeutic and side effects caused by modulating a particular drug target, as well as to discover biomarkers that serve as a surrogate measure on the effectiveness of target modulation.

A method using transcription factor activity profiling for drug target evaluation and or biomarker discovery is disclosed. The method comprises typically the following steps:
  a. Transfecting at least one type of model cells (primary cells or engineered cell lines) with a library (>2) of TF reporter vectors, with one population of cells transfected with one TF reporter vector that can recognize functional activity of a specific TF inside the cells.
  b. Measure reporter activities through fluorescence, luminescence or any appropriate techniques, in each population of cells, to evaluate the functional activity of the specific TF corresponding to the TF reporter vector being transfected in this particular population of cells.
  c. Construct a profile of the functional activities of all interested TFs
  d. If the reporter system used allow live cell analysis, treat the previous cells using appropriate methods to modulate a drug target of interests, repeat step i-iii, to obtain a second profile of TF activities in the same cells that are after drug target modulation. If the reporter used doesn't allow live cell analysis, start with a new batch of cells, apply appropriate methods to modulate the drug target of interests in these cells, then go through step i-iii to obtain a second profile of TF activities in cells that underwent target modulation.

e. Compare the first and second profiles to identify changes in functional activities of the TFs the type(s) of model cells due to modulating the said target Once the changes in TFs' functional activities are elucidated, one can further identify which pathways the drug target by identifying the affected TFs and the pathways they are linked to. One can also further predict the consequences of modulating this drug target by analyzing how the changes in TF activities would influence transcription and expression of relevant genes, and furthermore what therapeutic and toxic effects the changes in expression of the genes would lead to. Both the affected TFs and the downstream genes and proteins due to modulation of the drug target can be used as biomarkers, which can be used in preclinical and/or clinical studies as indications to effectiveness of therapeutic intervention and/or clinical safety.

Drug Evaluation Using TF Activity Profiling

Modern drugs are often designed to regulate one particular protein (drug target) with important roles in a pathological pathway. Most times, the drugs have in-target effects, which are the consequences of a successful modulation of the drug target (structurally or functionally), and off-target effects due to drugs' unintended influence on other proteins. Both the in-target and off-target effects often result in activation of a number of TFs mediated by signaling transduction. By analyzing the changes in TF activities in appropriate model cells before and after drug compounds treatment, it is possible to elucidate the therapeutic and side-effects of the drug compounds.

A method that uses transcription factor activity profiling for drug compound evaluation is disclosed. The method comprises typically the following steps:

a. Transfecting at least one type of model cells (primary cells or engineered cell lines) with a library (>2) of TF reporter vectors, with one population of cells transfected with one TF reporter vector that can recognize functional activity of a specific TF inside the cells.

b. Measure reporter activities through fluorescence, luminescence or any appropriate techniques, in each population of cells, to evaluate the functional activity of the specific TF corresponding to the TF reporter vector being transfected in this particular population of cells.

c. Construct a profile of the functional activities of all interested TFs d. If the reporter system used allow live cell analysis, treat the previous cells with the drug compound(s) of interests using appropriate methods, repeat step i-iii, to obtain a second profile of TF activities in the same cells that are after compound treatment. If the reporter used doesn't allow live cell analysis, start with a new batch of cells, treat these cells with the drug compound(s) of interests using appropriate methods, then go through step i-iii to obtain a second profile of TF activities in cells underwent compound treatment.

e. Compare the first and second profiles to identify changes in functional activities of the TFs in the type(s) of model cells due to treatment with the said drug compound(s)

Once changes in TF activities due to drug treatment are revealed, one can further identify which pathways were affected by the compound(s) by identifying the affected TFs and the pathways they are linked to. One can also further predict the consequences of compound treatment by analyzing how the changes in TF activities would influence transcription, thus expression of relevant genes, and furthermore what therapeutic and toxic effects the changes in transcription of the downstream genes would lead to. Both the TFs and the downstream genes and proteins affected by the drug treatment can be used as biomarkers to indicate to effectiveness of therapeutic intervention and/or clinical safety in preclinical and/or clinical studies.

Method to Predict Effects of a Stimulus in Human

By combining the transcription factor activity profiling method and bioinformatic techniques, we propose a novel method to predict therapeutic and toxic/safety effects of a stimulus in human. The stimulus can be exposure to chemicals, therapeutic agents and toxins, radiation, molecular intervention such as modulation of a drug target, and any other perturbations that can cause molecular and cellular responses by biological entities, including human and animals. The method comprises typically the following steps, Obtain changes in functional activities of at least 2 TFs in at least one type of model cells caused by a member of a set of reference stimuli whose effects in human are well characterized (such stimuli can be approved drugs, known toxins, etc.), using the method described previously.

a. Correlate the changes in the functional activities of the said TFs in the said model cells, with the known therapeutic and toxic/safety effects of the said reference stimuli in human b. Obtain changes in the functional activities of the said TFs in the same model cells caused by a test stimulus whose effects in human are not well characterized (such stimulus can be a new drug in development, a new toxin, etc.), using the method(s) described previously in section 2.b.

c. Compare the changes in TFs' functional activities in the said model cells caused by the test stimulus and the changes in TF functional activities caused by the reference stimuli, identify possible similarities among the changes, correlate the similarities with the therapeutic and toxic/safety effects of the reference stimuli in human to predict the therapeutic and toxic/safety effects of the test stimulus in human.

Method for Determining Transporter Proteins

Influencing Drug Transportation

Transporter proteins are a family of membrane proteins that are responsible for transporting a variety of substances (small molecule drugs, ions, peptides, etc.) in and out of cells. They play key roles in drug absorption, distribution and excretion. Being able to profile which transporter proteins affect transportation of a drug compound in and out of cells can be very useful in characterizing the compound's ADME or pharmacokinetic properties and in providing mechanistic insights on how to improve the compound's ADME/PK properties.

A commonly used in vitro method to study transportation of a compound is to study how the test compound is transported through a cell monolayer grown on a porous membrane. This transcellular transport analysis method can be readily realized using the previously disclosed transfection devices that allow formation of confluent cell monolayers on a porous membrane inside each transfection unit. By combining cell transfection and transcellular transport analysis, we come up with a novel method to evaluate influence of individual transporters on a test compound's ADME/PK properties.

The method comprises typically the following steps,
a. Grow an appropriate model cells into confluent monolayers on porous membranes in an array of applicable devices. The model cells must be able to grow into confluent monolayer with tight junctions formed among adjacent cells, and the model cells have low native expression level of transporter proteins. MDCK cell line is a good candidate as it meets both requirements.
b. Transfect the cells with a library of DNA plasmids using applicable methods. The cells in each device are transfected with one type of DNA plasmids that encode a specific transporter protein. As a result, an array of testing cell monolayers is created with each cell monolayer expressing a particular transporter protein.
c. Use applicable analytical methods to measure a test compound's permeability to every cell monolayer expressing the known transporter protein, compare with the reference permeability of the said compound to the wild-type model cells to identify all the individual transporter proteins that affect the permeability of the said compound to the model cell monolayers and the relative significance of their influence.

Once the individual transporter proteins that affect the compound's transportation are identified, one can analyze which individual transporter-compound interaction improve and which deteriorates the compound's ADME/PK properties. This information can be very valuable to guide compound optimization to modify compound structure so that it becomes the substrate of particular transporter proteins to render the compound desirable ADME/PK properties or therapeutic effects. For example, many influx transporters such as PEPT1, ASBT, OATP-B, etc. help improve drug absorption, while efflux transporters such as P-gp, MRP2 and BCRP play the opposite role. Therefore, if a compound is identified to the substrate of particular efflux transporters, one can modify the compound structure to avoid binding to the efflux transporters, furthermore, to transform the compound as the substrate of some influx transporters, thus improving the absorption properties of the drug compound.

Another example is to optimize compound structure for targeted drug delivery. The strategy is to focus on differential expression of transporters between the target cells/organ and other cells/organs. The information obtained from compound-transporter interaction profiling can help guide structural optimization for compound so that it is absorbed only by the target cells/organ.

Another valuable application of the method is in drug toxicity prediction. There are many transporters only expressed in particular organs, for example, NTCP is a transporter exclusively expressed in liver, a drug compound that is the substrate of NTCP transporter is more likely to have liver toxicity due to the high chance of being delivered to liver. Similarly, a drug that is the substrate of blood-brain barrier (BBB)-specific transporters is more likely to penetrate BBB to reach brain, thus has higher possibility of causing neurotoxicity.

Method to Predict Compound's ADME/PK Properties

By combining the compound-transporter interaction profiling method and bioinformatic techniques, we propose a novel method to predict a compound's ADME/PK properties. The method comprises typically the following steps, a. Obtain the profiles on the interactions of each member of a reference compound library with a library (>2) of transporter proteins in at least one type of model cells, using the method described previously in section 2.e. The reference compounds are approved or failed drugs whose ADME/PK properties in human are well characterized.
b. Correlate the compound-transporter interaction profiles in the said model cells, with the ADME/PK properties of the said reference compounds
c. Obtain the profile on the interactions of a test drug compound with the library of transporter proteins in the same model cells, using the method described previously in section 2.e.
d. Compare the profiles on transporter interaction in the said model cells among the test compound and the reference compounds, identify possible similarities, correlate the similarities with the ADME/PK properties of the reference compounds in human to predict the ADME/PK properties of the test compound in human.

I claim:
1. A cell transfection apparatus comprising:
a culture device having a first plate joined to a second plate, and a porous membrane fixed between the first and second plates, the first plate having a plurality of openings aligned with a plurality of openings in the second plate that together define wells having a first chamber and a second chamber separated by the porous membrane, each of the first chambers being configured to receive and confine a population of host cells; and
at least two sets of electrodes, wherein one of the sets is aligned above the culture device, and another set is aligned below the culture device, and wherein the two sets are individually controlled to provide a unidirectional current flowing across the porous membrane.

2. The cell transfection apparatus of claim 1, wherein the wells are arranged in rows and columns.

3. The cell transfection apparatus of claim 2, wherein the plate has a 96 well or 384 well plate format.

4. The cell transfection apparatus of claim 1, wherein each electrode of at least one set of electrodes is individually controllable.

5. The cell transfection apparatus of claim 1, wherein each electrode of at least one set of electrodes corresponds to one and only one well of said plate.

6. The cell transfection apparatus of claim 1, wherein a user control is provided to receive a user input that controls the direction of the unidirectional current flow.

7. A method for transfecting a population of host cells, comprising:
(i) providing a cell transfection apparatus comprising:
(a) a culture device having a first plate joined to a second plate, and a porous membrane fixed between the first and second plates, the first plate having a plurality of openings aligned with a plurality of openings in the second plate that together define wells having a first chamber and a second chamber separated by the porous membrane each of the first chambers being configured to receive and confine a population of host cells that are adhered to the porous membrane; and
(b) at least two sets of electrodes, wherein one of the sets is aligned above the culture device, and another set is aligned below the culture device, and wherein the two sets are individually controlled to provide a unidirectional current flowing across the porous membrane; and
(ii) running said current across the porous membrane.

8. The method of claim 7, wherein the wells are arranged in rows and columns.

9. The method of claim 8, wherein the plate has a 96 well or 384 well plate format.

10. The method of claim 7, wherein each electrode of at least one set of electrodes is individually controllable.

11. The method of claim 7, wherein each electrode of at least one set of electrodes corresponds to one and only one well of said plate.

12. The method of claim 7, wherein the direction that the current is run is selected based on the host cells.

* * * * *